United States Patent [19]

Yajima et al.

[11] Patent Number: 5,059,679

[45] Date of Patent: Oct. 22, 1991

[54] METHOD OF SELECTIVELY SULFATING PEPTIDES

[75] Inventors: Haruaki Yajima; Nobutaka Fujii, both of Ohsaka; Shinya Kiyama, Kanagawa, all of Japan

[73] Assignee: Shin-Etsu CHemical Co., Ltd., Tokyo, Japan

[21] Appl. No.: 331,292

[22] Filed: Mar. 30, 1989

[30] Foreign Application Priority Data

Mar. 31, 1988 [JP] Japan .................................. 63-80116

[51] Int. Cl.$^5$ .......................... A61K 37/02; C07K 1/00
[52] U.S. Cl. .................................... 530/335; 530/336; 530/345; 530/324; 530/338
[58] Field of Search ............... 530/335, 336, 345, 324, 530/338

[56] References Cited

PUBLICATIONS

Kurano et al., J. Chem. Soc. Chem. Commun. (1987) 323–325.

Primary Examiner—John Doll
Assistant Examiner—Bennett Celsa
Attorney, Agent, or Firm—McAulay Fisher Nissen Goldberg & Kiel

[57] ABSTRACT

The invention provides a method and reagent for the modification of polypeptides useful in experimental research in the area of genetic engineering starting from a polypeptide such as hCCK-33 in an unsulfated form which contains Tyr and Ser and/or Thr residues by first protecting the amino-groups in the starting polypeptide, masking the OH-groups in the Ser and/or Thr residues and selectively sulfating the OH-groups in the Tyr residues after deprotection.

4 Claims, No Drawings

METHOD OF SELECTIVELY SULFATING PEPTIDES

BACKGROUND OF THE INVENTION

The present invention relates to a method for the preparation of a polypeptide, more particularly it relates, to a method for the preparation of a polypeptide by the selective sulfation of OH-groups of Tyr in a starting material having Tyr, Ser and/or Thr residues.

Recently, polypeptides have drawn enthusiastic attention as a type of protein useful in genetic engineering. Synthesis of various types of polypeptides has been hitherto attempted. The synthetic methods hitherto proposed include the solid phase method and the liquid phase method. The former method is not suitable as an industrial method of preparation because of the low purity of the resultant peptide and the many difficulties encountered in the final stage of purification. The liquid phase method, on the other hand, is further classified into the stepwise method and the fragment condensation method, the latter of which is currently used to avoid the difficulty in the purification of the product unavoidable in the former method as in the solid phase method.

The fragment condensation method has several advantages as compared to the step-wise method. Namely, the synthesis can be formed fragment by fragment and the loss of product can be decreased. In addition, the final product is easily formed and has a high purity. However, the fragment condensation method is accompanied by the possibility that the amino acid residue of the carbon terminal is susceptible to racemization in the condensation reaction. This racemization detracts from the advantages of the fragment condensation method. It can be partially solved by appropriate selection of the combination of the fragments as is known in the art.

Success has hitherto not been reported in the attempts for the total synthesis of human cholecystokinin, referred to as hCCK-33 hereinbelow, as a polypeptide by the fragment condensation method. The reason for the unsuccessful outcome is because a reagent is not available for the selective sulfation of the Tyr residues alone in the presence of amino acid residues such as Ser and Thr when successive azide condensation reaction is attempted on a plural number of fragements having protective groups and that the sulfation by a reagent occurs not on the desired Tyr-OH but preferentially on the Ser-OH or Thr-OH.

SUMMARY OF THE INVENTION

The inventors have conducted extensive studies in connection with the above described problems and, as a result, have arrived at a discovery of a reagent and method by which amino groups susceptible to the elimination of the protective groups and Tyr residues can be selectively sulfated in a basic condition leading to the completion of the present invention.

The scope of the present invention accordingly is to provide a novel method for the preparation of a polypeptide using a starting polypeptide having Ser and/or Thr residues according to which the amino groups of the starting polypeptide are protected with protective groups for amino groups capable of being eliminated in a basic condition and the OH groups in the Ser and/or Thr residues are masked followed by elimination of the protective groups to effect selective sulfation of the OH groups of the Tyr residues.

BRIEF DESCRIPTION OF THE DRAWING

FIG. 1 is a flow chart illustrating the synthetic route of human cholecystokinin having a protective group.

FIG. 2 is a flow chart illustrating the synthetic route of C-terminated decapeptideamide having a protective group.

FIG. 3 is a graph showing tert-butyldiphenylsilylation of Ser and Tyr.

FIG. 4 is a graph showing sulfation of Z(OMe)-Tyr-OMe and Z(OMe)-Ser-OMe using a pyridine-$SO_3$ complex or pyridinium acetyl sulfate in a DMF-pyridine mixture.

FIG. 5 is a flow chart illustrating conversion of unsulfated hCCK-33 into sulfated hCCK-33.

FIG. 6 is a graph showing the increase in the protein release from a pancreas responding to CCK-peptide in an anesthetized dog.

FIG. 7 is an elution diagram in the ion-exchange chromatography in the course of HPLC purification of unsulfated hCCK-33.

FIG. 8 is an elution diagram in the ion-exchange chromatography in the courses of CM- and HPLC-purification of sulfated hCCK-33.

DETAILED DESCRIPTION OF THE PREFERRED EMBODIMENTS

The present invention provides a novel method for the preparation of a polypeptide. The method is characterized by the selective sulfation of OH-groups of Tyr residues in a polypeptide containing Tyr residues and Ser and/or Thr residues as the starting material. The sulfating method comprises successive steps of protecting amino-groups in the polypeptide as the starting material with amino-protective groups capable of being eliminated in a basic condition and selectively sulfating the OH-groups in Tyr after deprotection, which means elimination of the protective group, of the amino-groups followed by masking of the OH-groups in the Ser and/or Thr residues.

The invention is described in detail in the following.

Each of the amino acids used in the invention is the L-type optical isomer excepting glycine and, in the following, expressed by an abbreviation composed of three Roman characters according to the conventional usage. Other abbreviations appearing in the following description each denote the chemical compound or group shown below.

Bzl: benzyl
CHA: cyclohexylamine
Chp: cycloheptyl
$Cl_2$-Bzl: 2,6-dichlorobenzyl
DCHA: dicyclohexyl amine
DMF: dimethyl formamide
DMSO: dimethyl sulfoxide
EDT: ethane dithiol
Fmoc: 9-fluorenyl methyl oxycarbonyl
HMPA: hexamethyl phosphonamide
Mts: mesitylene-2-sulfonyl
NMM: N-methyl morpholine
(O): sulfoxide
Su: N-hydroxy succinimidyl
TEA: triethyl amine
TFA: trifluoroacetic acid
THF: tetrahydrofuran
TMSOTf: trimethylsilyl trifluoromethane sulfonate tBuPh2Si: tert-butyl diphenyl silyl
tBuMe2Si: tert-butyl dimethyl silyl
Me3Si: trimethyl silyl
Z: benzyloxy carbonyl
Z(OMe): p-methoxybenzyloxy carbonyl In the method of the invention, a polypeptide having Tyr residues and Ser and/or Thr residues is used as the starting material and human cholecystokinin (hCCK-33) in the unsulfated form is an example thereof.

Accordingly, the description of the invention will be given with particular reference to the synthesis of hCCK-33 by way of the fragment condensation method as a typical example.

The method of the invention comprises following three steps including the first step for the synthesis of a hCCK-33 having protective groups, the second step for obtaining an unsulfated hCCK-33 by the elimination of the protective groups and the third step for the selective sulfation of the Tyr residues.

In the first step, a hCCK-33 having protective groups is synthesized as shown in FIG. 1 by the successive condensation reaction of the seven polypeptide fragments shown below by the azide method according to the flow chart given in FIG. 1.

(1) H-Asp(OChp)-Arg(Mts)-Asp(OChp)-Tyr-Met(O)-Gly-Trp(Mts)-Met(O)-Asp(OChp)-Phe-NH2
(2) Z(OMe)-His-Arg(Mts)-Ile-Ser-NHNH2
(3) Z(OMe)-Asp(OBzl)-Pro-Ser(Bzl)-NHNH2
(4) Z(OMe)-Asn-Leu-Gln-Asn-Leu-NHNH2
(5) Z(OMe)-Ser(Bzl)-Ile-Val-Lys(Z)-NHNH2
(6) Z(OMe)-Gly-Arg(Mts)-Met(O)-NHNH2
(7) Z(OMe)-Lys(Z)-Ala-Pro-Ser-NHNH2

The fragment (1) mentioned above is obtained, as shown in FIG. 2, by the condensation of Z(OMe)-Tyr(Cl2-Bzl)-OH with TFA-treated sample of Z(OMe)-Met(O)-Gly-Trp(Mts)-Met(O)-Asp(OChp)-Phe-NH2 by the Su-ester method first using Tyr(Cl2-Bzl).

When successive condensation of each of the fragments was undertaken starting from the C-terminated decapeptideamide (1) (sites 24 to 33) obtained by the method of FIG. 2, each of the fragments was dissolved in a mixture of DMF-DMSO-HMPA (1:1:1) and 1.5 to 5 equivalents of the acyl component were used to ensure completion of the reaction. Each of the reactions proceeded smoothly without peracylation despite the use of an excessive amount of the acyl component. After completion of the reaction, the excessive amount of the acyl component was removed by the reprecipitation method or gel filtration method to effect purification. Table 1 below shows the amino acid compositions in the hydrolysis products of the hCCK-33, unsulfated hCCK-33 and protected intermediates with 6N hydrochloric acid. The experiments leading to these results have established the synthetic route for the protected hCCK-33.

TABLE 1

| Amino acid | Peptide having protective groups | | | | | | | Unsulfated hCCK-33 | Sulfated hCCK-33 |
|---|---|---|---|---|---|---|---|---|---|
| | 24–33 | 20–33 | 17–33 | 12–33 | 8–33 | 5–33 | 1–33 | | |
| Asp | 2.81 | 3.09 | 4.04 | 5.71 | 5.82 | 5.74 | 6.53 | 5.72 | 5.77 (6)*** |
| Ser | | 0.87 | 1.87 | 1.57 | 2.52 | 2.30 | 3.69 | 3.62 | 3.62 (4) |
| Glu | | | | 1.03 | 1.07 | 0.92 | 1.24 | 1.11 | 1.05 (1) |
| Pro | | | 0.90 | 0.89 | 0.92 | 0.91 | 2.32 | 2.02 | 1.71 (2) |
| Gly | 1.11 | 1.28 | 1.11 | 1.29 | 1.28 | 2.28 | 2.57 | 2.18 | 2.09 (2) |
| Ala | | | | | | | 1.20 | 1.11 | 1.00 (1) |
| Val | | | | | 0.78 | 0.70 | 0.81 | 0.73 | 0.71 (1) |
| Met* | 1.71 | 1.66 | 1.82 | 1.78 | 1.67 | 2.33 | 2.67 | 2.53 | 2.86 (3) |
| Ile | | 1.08 | 0.97 | 0.91 | 1.69 | 1.09 | 1.76 | 1.49 | 1.67 (2) |
| Leu | | | | 1.89 | 1.99 | 1.69 | 2.21 | 2.10 | 2.05 (2) |
| Tyr | 0.92 | 1.05 | 1.04 | 1.02 | 1.05 | 1.03 | 1.05 | 0.91 | 0.94 (1) |
| Phe | 1.00 | 1.00 | 1.00 | 1.00 | 1.00 | 1.00 | 1.00 | 1.00 | 1.00 (1) |
| Lys | | | | | 0.81 | 0.78 | 2.10 | 1.75 | 2.11 (2) |
| His | | 0.97 | 0.94 | 0.80 | 0.75 | 0.68 | 0.73 | 0.75 | 0.87 (1) |
| Trp** | 0.96 | 0.86 | 0.86 | 0.85 | 0.72 | 0.87 | 0.85 | N.D. | N.D. |
| Arg | 0.96 | 2.17 | 1.96 | 1.98 | 2.06 | 2.96 | 3.20 | 2.69 | 3.11 (3) |
| Recovery | 80% | 89% | 79% | 77% | 82% | 95% | 84% | 84% | 79% |

*Met + Met (0).
**Hydrolysis with 4N MeSo3H.
***Theoretical values shown in ()

The unsulfated hCCK-33 was obtained in the second step by eliminating all of the protective groups from the protected hCCK-33. The Met(O) residues were reduced to Met prior to the elimination of the protective groups by the treatment with phenylthio trimethyl silane and all of the protective groups were removed by processing the reduced peptide with TMSOTf-thioanisole/TFA. The peptide freed from the protective groups was subjected to gel filtration using Sephadex G-25 and subjected to ion-exchange chromatography on a CM-Trisacryl M using a ammonium hydrogen carbonate buffer solution as the eluant. The homogeneity of the unsulfated hCCK-33 obtained by the synthesis could be confirmed by the amino acid analysis and HPLC using a reversedphase chromatographic column after hydrolysis with 6N hydrochloric acid.

Then, several simulation experiments were undertaken for Tyr, Ser, Trp, Met, His and Lys prior to the selective sulfation of the Tyr residual groups in the third step.

The inventors discovered from these simulation experiments that Ser-OH groups were silylated at a much higher rate than Tyr-OH groups. tBuPh2Si chloride was selected as the silylating agent on the base of the discovery that Ser(tBuPh2Si) derivatives remained intact at the time of 24 hours from the start of the sulfation carried out under the condition using a pyridine-SO3 complex in contrast to Ser(Me3Si) derivatives and Ser(tBuMe2Si) derivatives which were decomposed. Silylation of Z(OMe)-Ser-OMe with tBuPh2Si chloride proceeded quantitatively within 30 minutes in the presence of imidazole. On the other hand, it was found that the partial silylation of Tyr-OH which proceeded under similar conditions could be suppressed by the addition of a phenolic compound under cooling with ice. Phenol gave the most satisfactory results among the three kinds of phenolic compounds used in the test.

As is shown in FIG. 3, silylation of Tyr-OH is suppressed from 46% to 31% after 4 hours by the addition of 20 equivalents of phenol. Decomposition of tBuPh$_2$Si groups by a simple processing at 0° C. for 60 minutes using 1M tetrabutyl ammonium fluoride Bu$_4$NF in DMF is known but, on the contrary, Tyr(SO$_3$H) has been found as stable even by this hard base treatment. Inspection by the thin layer chromatography (TLC) indicated that His, Mrt and Trp remained unchanged even after being kept under the conditions of silylation and de-silylation. A conclusion was obtained from these simulation experiments that the selective sulfation of Tyr-OH groups in the presence of Ser-OH was effected by the reversible masking of OH-groups of Ser-OH by the tBuPh$_2$Si groups. Thr is not contained in hCCK-33.

The Fmoc group, which has been reported by Carpino and Han in 1970 as an amino protective group capable of being eliminated with a base, proved to be decomposed together with the tBuPh$_2$Si groups by the treatment with 1M Bu$_4$NF in DMF so that α- and ε-amino functional groups in the two Lys residues (sites 1 and 11) were masked with the Fmoc groups prior to sulfation in the inventive method. It was found in the inspection by undertaking TLC that the partial acylation of Tyr by Fmoc-OSu was effectively suppressed by the addition of phenol.

Recently, pyridinium acetyl sulfate (PAS reagent) has been proposed as a sulfation reagent by Penke et al. This reagent was used for the preparation of swine CCK-33 in DMF-pyridine by Penke et al. and in TFA by Kurano et al. after masking of Ser-OH with acetyl groups or phenoxyacetyl groups, respectively.

Sulfation of Tyr residues was carried out in the invention under a basic condition in consideration of the instability of Tyr(SO$_3$H) in acid and the presence of unmasked Trp residues contained in the unsulfated hCCK-33 in the inventive method. The pyridine-SO$_3$ complex could sulfate Z(OMe)-Tyr-OMe more easily than the PAS reagent in the presence of pyridine in DMF (see FIG. 4). Similar tendency was also found in the sulfating reaction of Z(OMe)-Ser-OMe. Partial sulfation, i.e. 32% sulfation after 4 hours, of His by a pyridine-SO$_3$ complex was shown by the inspection with TLC but His was regenerated quantitatively within 60 minutes by the addition of water. Use of EDT was effective in suppressing the partial oxidation of Met and change of Trp during sulfation. FIG. 4 shows sulfation of Z(OMe)-Tyr-OMe and Z(OMe)-Ser-OMe with a pyridine-SO$_3$ complex or pyridinium acetyl sulfate in DMF-pyridine.

After these simulation experiments, the aforementioned hCCK-33 in the unsulfated form was converted into sulfated hCCK-33 by being successively subjected to the following reactions as shown in FIGS. 1 and 5.

(1) All of the amino-functional groups were protected by the treatment at 0° C. for 2 hours with Fmoc-OSu in the presence of TEA. Phenol was added to protect the Tyr residues.

(2) Four Ser-OH functional groups were preferentially protected by a treatment with tBuPh$_2$Si-Cl in the presence of imidazole at 4° C. taking a longer time of 14 hours than in the simulation experiments. Phenol was added to minimize silylation of the Tyr residues.

(3) Tyr-OH was sulfated by a treatment with a pyridine-SO$_3$ complex in DMF containing 20% pyridine at 25° C. taking 24 hours followed by the addition of EDT to protect Met and Trp.

(4) The tBuPh$_2$Si protective groups and Fmoc protective groups were eliminated by a treatment with 1M Bu$_4$NF in DMF at 4° C. taking 1 hour and then at 25° C. taking another 1 hour. Dibenzofulvene derived from Fmoc groups was quenched by the addition of EDT.

The crude sample of hCCK-33 thus sulfated was subjected to ion-exchange chromatography on CM-Trisacryl M using the gradient elution method with a 0.2M NH$_4$HCO$_3$ buffer solution and then purified by HPLC through an Asahi Pak ODP-50 column by isocratic elution using 32% MeCN in a 0.1M AcONH$_4$ solution. The former purification method was effective to remove the excessively sulfated hCCK and the unsulfated hCCK. Separation of the desired product was more satisfactory by using this HPLC column than by using the YMC-DOS 302 column. The overall yield was 15% as calculated on the base of the unsulfated hCCK-33. The yield seemed to be inherently dependent on the conditions in the silylation. A yield of 13% was obtained by the silylation at 25° C. for 3 hours although no optimum conditions for the silylation have yet been established.

The purity of the thus obtained synthetic hCCK-33 was determined by the analytical HPLC and the amino acid assay after acid hydrolysis. Presence of Tyr(SO$_3$) was confirmed by the leucine-aminopeptidase (LAP) digestion.

The synthetic hCCK-33 was concurrently subjected to the bioassay with synthetic hCCK-8 to determine the activity. The bioassay was carried out by measuring the blood flow in the pancreas capillary vessel and the protein release from pancreas using a group of four mongrel dogs anesthesized with pentobarbital. The blood flow in the pancreas capillary vessel was measured using a laser-Doppler perfusion monitor and the protein concentration in the pancreas was determined according to the method of O. H. Lowry, N. J. Rosebrough, A. L. Farr and R. J. Randall, J. Biol. Chem. 193, 265 (1951).

Bolus injections of 1.0, 3.125, 6.25, 12.5, 25, 50, 100 and 200 picomoles per kg body weight of the synthetic hCCK-33 and CCK-8 were given through a femoral vein catheter each at an interval of 60 minutes. Pancreas blood flow was increased in parallel with the dose of the synthetic hCCK-33 administrated. The protein release from pancreas was also increased in parallel with the dose of the synthetic hCCK-33 administrated. The increasing effect could be noted even with the lowest dose of 3.125 picomoles/kg and the highest effect was obtained with the dose of 200 picomoles/kg. The activity of the synthetic hCCK-33 was 92% of that of the synthetic CCK-8 on the molar basis in respect of the effects on the blood flow in the pancreas capillary vessel and the protein release from pancreas. In respect of the gastric juice, pepsin release and pancreas secretion in the living samples of rats, the synthetic hCCK-33 was about two to three times more active than the CCK-8 on the molar basis. In respect of stimulation to the pepsinogen secretion from excised gastric tissues of guinea pigs, the activity of the synthetic hCCK-33 was about the same as the CCK-8 on the molar basis. CCK-8 was 2.5 times more active than the whole molecules of swine CCK-33. Consequently, it is a conclusion that the activity of the synthetic hCCK-33 according to the invention is comparable with or even higher than the activity of the natural swine CCK-33. Since the ratio of the activity of the unsulfated hCCK-33 to the activity of CCK-8, taken as unity on the molar basis, was 0.074 in the aforementioned assay with dogs, it was concluded that an important role is played by the sulfated sites in the molecules having influences on the in vivo activity of CCKs.

FIG. 6 illustrates the increase in the protein release from pancreas of an anesthetized dog in response to these 3 kinds of CCK-peptides.

Differently from the synthesis of the swine CCK-33 reported by Penke or Kurano et al., products of highly active hCCK-33 can be obtained according to the present invention by avoiding contacting of the peptide with a strong base.

EXAMPLE

In the following, the method of the present invention is described in more detail by way of an example for the synthesis of human cholecystokinin hCCK-33.

The $R_f$-values appearing in the following description were obtained by the thin layer chromatography (TLC) on silica gel (Kieselgel G manufactured by Merck Co.) using the following solvent mixtures, respectively.

$R_{f1}$: $CHCl_3$-MeOH-$H_2O$ (8:3:1)
$R_{f2}$: n-BuOH-AcOH-pyridine-$H_2O$ (4:1:1:2)
$R_{f3}$: n-BuOH-AcOH-AcOEt-$H_2O$ (1:1:1:1)

The color intensity by the ninhydrin reaction was determined using a Shimadzu Dual Wavelength TLC Scanner Model CS-900. The Fab-MS spectra were obtained using an FAB ion source and a double-convergence mass spectrometer Model JEOL JM HX-100. The LAP was Lot No. L-6007 purchased from Sigma Co. and the CCK-8 was purchased from Protein Research Laboratory. HPLC was performed using Waters Model 204. The blood flow in pancreas capillary vessel was monitored using a laser-Doppler perfusion monitor (Model LD 5000 manufactured by Seattle Model Pacific Co., Wash., U.S.A.).

The term of "washing treatment" appearing in the following description means, unless otherwise mentioned, a process including the successive steps of evaporation of the solvent from the sample, treatment of the residue with a 5% citric acid solution and ether, washing of the thus obtained powder successively with a 5% citric acid solution, 5% $NaHCO_3$ solution and water and recrystallization or precipitation from a suitable solvent.

(1) Preparation of Z(OMe)-Tyr($Cl_2$-Bzl)-Met(O)-Gly-Trp(Mts)-Met(O)-Asp(OChp)-Phe-$NH_2$ [1] (sites 27 to 33)

Z(OMe)-Met(O)-Gly-Trp(Mts)-Met(O)-Asp(OChp)-Phe-$NH_2$ in an amount of 4.57 g (3.63 millimoles) treated with TFA was dissolved in 25 ml of DMF containing 0.51 ml (1 equivalent) of TEA and then admixed with 2.62 g (1.2 eqivalents) of Z(OMe)-Tyr($Cl_2$-Bzl)-OSu and 0.40 ml (1 equivalent) of NMM and the mixture was stirred overnight. The product was purified by the washing treatment and succeeding precipitation from DMF containing AcOEt. The yield of the product having $R_{f1}$ of 0.64 was 5.26 g corresponding to 92% of the theoretical value. The physical parameters and the analytical data are shown in Table 2 along with those of the protected intermediates.

(2) Preparation of Z(OMe)-Asp(OChp)-Tyr($Cl_2$-Bzl)-Met(O)-Gly-Trp(Mts)-Met(O)-Asp(OChp)-Phe-$NH_2$ [1] (sites 26 to 33).

The sample 4.95 g (3.13 m moles) of the aforementioned peptideamide with 7-membered residues after a treatment with TFA was dissolved in 30 ml of DMF containing 0.43 ml (1 equivalent) of TEA and admixed with Z(OMe)-Asp(OChp)-OSu prepared from 2.70 g (1.5 equivalents) of DCHA salt in 15 ml of THF and 0.41 ml (1.2 equivalents) of NMM and the mixture was stirred overnight. The product was purified by the washing treatment followed by precipitation from DMF containing AcOEt. The yield of the product having $R_{f1}$ of 0.75 was 5.23 g corresponding to 90% of the theoretical value.

(3) Preparation of Z(OMe)-Arg(Mts)-Asp(OChp)-Tyr($Cl_2$-Bzl)-Met(O)-Gly-Trp(Mts)-Met(O)-Asp(OChp)-Phe-$NH_2$ [1] (sites 25 to 33)

The sample (4.75 g or 2.65 m moles) of the aforementioned peptideamide with 8-membered residues after a treatment with TFA was dissolved in 30 ml of DMF containing 0.37 ml (1 equivalent) of TEA and admixed with Z(OMe)-Arg(Mts)-OSu prepared from 3.28 g (2 equivalents) of CHA salt in 20 ml of THF and 0.35 ml (1.2 equivalents) of NMM and the mixture was stirred overnight. The product was purified by the washing treatment followed by precipitation from DMF containing AcOEt. The yield of the product having $R_{f1}$ of 0.78 was 4.15 g corresponding to 74% of the theoretical value, (4) Preparation of Z(OMe)-Asp(OChp)-Arg(Mts)-Asp(OChp)-Tyr-($Cl_2$-Bzl)-Met(O)-Gly-Trp(Mts)-Met-(O)-Asp(OChp)-Phe-$NH_2$ [1] (sites 24 to 33)

The sample (4.15 g or 1.95 m moles) of the aforementioned peptideamide with 9-membered residues after a treatment with TFA was dissolved in 40 ml of DMF containing 0.27 ml (1 equivalent) of TEA and admixed with Z(OMe)-Asp(OChp)-OSu prepared from 1.68 g (1.5 equivalents) of DCHA salt in 15 ml of THF and 0.26 ml (1.2 equivalents) of NMM and the mixture was stirred for 18 hours. The product was purified by the washing treatment followed by precipitation from DMF containing MeOH. The yield of the product having $R_{f1}$ of 0.70 was 3.57 g corresponding to 78% of the theoretical value.

TABLE 2

| Peptide protected with Z(OMe)- (sites) | Melting point °C. | $[\alpha]_D^{20}$ (DMF) | Empirical formula | Elementary analysis, calculated (found) | | |
|---|---|---|---|---|---|---|
| | | | | C | H | N |
| 7 residues (27–33) | 215–218 | −20.4° | $C_{77}H_{91}N_9$ $O_{17}S_3Cl$ | 58.47 (58.17 | 5.80 5.96 | 7.97 7.98) |
| 8 residues (26–33) | 200–202 | −23.9° | $C_{88}H_{108}N_{10}$ $O_{20}S_3Cl_2$ | 58.95 (58.66 | 6.07 6.37 | 7.81 7.79) |
| 9 residues (25–33) | 238–243 | −21.9° | $C_{103}H_{130}N_{14}$ $O_{23}S_4Cl_2H_2O$ | 57.55 (57.52 | 6.19 6.31 | 9.12 9.27) |
| 10 residues [1] (26–33) | 230–233 | −13.5° | $C_{114}H_{147}N_{15}$ $O_{26}S_4Cl_2$ | 58.45 (58.48 | 6.32 6.42 | 8.97 8.94) |

(5) Preparation of Z(OMe)-His-Arg(Mts)-Ile-Ser-Asp(OChp)-Arg(Mts)-Asp(OChp)-Tyr($Cl_2$-Bzl)-Met-(O)-Gly-Trp(Mts)-Met(O)-Asp(OChp)-Phe-$NH_2$ (sites 20 to 33)

An azide form product prepared from 7.99 g (2 equivalents) of the fragment [2] in 40 ml of DMF and 0.61 ml (1.2 equivalents) of NMM were added to a solution of 10.73 g (4.58 m moles) of the fragment [1] after a treatment with TFA in 40 ml of DMF under cooling with ice and the mixture was stirred overnight. The product was purified by the washing treatment followed by precipitation from DMF containing MeOH. The yield of the product having $R_{f1}$ of 0.73 was 11.99 g corresponding to 87% of the theoretical value.

Table 3 below shows the physical parameters and the results of elementary analysis together with the data for other peptides having protective groups.

(6) Preparation of Z(OMe)-Asp(OBzl)-Pro-Ser(Bzl)-His-Arg(Mts)-Ile-Ser-Asp(OChp)-Arg(Mts)-Asp(OChp)-Tyr(Cl$_2$-Bzl)Met(O)-Gly-Trp(Mts)-Met(O)-Asp(OChp)-Phe-NH$_2$ (sites 17 to 33)

An azide form product prepared from 3.46 g (1.5 equivalents) of the fragment [3] in 10 ml of DMF and 0.52 ml (1.2 equivalents) of NMM were added to a solution of the above mentioned peptideamide of 17-membered residues after a treatment with TFA in 30 ml of DMF under cooling with ice and the mixture was stirred overnight. The product was purified by the washing treatment followed by precipitation from DMF containing AcOEt. The yield of the product having $R_{f1}$ of 0.71 was 8.64 g corresponding to 63% of the theoretical value.

(7) Preparation of Z(OMe)-Asn-Leu-Gln-Asn-Leu-Asp(OBzl)-Pro-Ser(Bzl)-His-Arg(Mts)-Ile-Ser-Asp(OChp)-Arg(Mts)-Asp(OChp)-Tyr(Cl$_2$-Bzl)-Met(O)-Gly-Trp(Mts)-Met(O)-Asp(OChp)-Phe-NH$_2$ (sites 12 to 33)

An azide form product prepared from 7.57 g (4 equivalents) of the fragment [4] in 90 ml of DMF-DMSO-HMPA (1:1:1) and 0.41 ml (1.2 equivalents) of TEA were added to a solution of 8.50 g (2.43 m moles) of the above mentioned amide of 17-membered residues after a treatment with TFA in 30 ml of DMF containing 0.34 ml (1 equivalent) of TEA under cooling with ice and the mixture was stirred for 48 hours. The product was purified by the gel filtration method with Sephadex LH-60 followed by precipitation from DMF containing AcOEt. The yield of the product having $R_{f1}$ of 0.73 was 4.84 g corresponding to 49% of the theoretical value.

(8) Preparation of Z(OMe)-Ser(Bzl)-Ile-Val-Lys(Z)-Asn-Leu-Gln-Asn-Leu-Asp(OBzl)-Pro-Ser(Bzl)-His-Arg(Mts)-Ile-Ser-Asp(OChp)-Arg(Mts)-Asp(OChp)-Tyr(Cl$_2$-Bzl)-Met(O)-Gly-Trp(Mts)-Met(O)-Asp(OChp)-Phe-NH$_2$ (sites 8 to 33)

An azide form product (2.10 g or 4 equivalents) prepared from the fragment [5] in 20 ml of DMF and 0.10 ml (1.2 equivalents) of TEA was added to a solution of 2.53 g (0.62 m moles) of the above mentioned peptideamide of 22-membered residues after a treatment with TEA in 10 ml of DMF containing 0.086 ml (1 equivalent) of TEA under cooling with ice and the mixture was stirred overnight. The product was purified by the gel filtration method with Sephadex LH-60 followed by precipitation from DMF containing AcOEt. The yield of the product having $R_{f1}$ of 0.63 was 1.95 g corresponding to 67% of the theoretical value.

(9) Preparation of Z(OMe)-Gly-Arg(Mts)-Met(O)-Ser(Bzl)-Ile-Val-Lys(Z)-Asn-Leu-Gln-Asn-Leu-Asp(OBzl)-Pro-Ser(Bzl)-His-Arg(Mts)-Ile-Ser-Asp(OChp)-Arg(Mts)-Asp(OChp)-Tyr(Cl$_2$-Bzl)-Met(O)-Gly-Trp(Mts)-Met(O)-Asp(OChp)-Phe-NH$_2$ (sites 5 to 33)

An azide form product (0.98 g or 4 equivalents) prepared from the fragment [6] in 5 ml of DMF and 0.15 ml (4 equivalents) of NMM was added to a solution of 1.51 g (0.33 m moles) of the above mentioned peptide of 26-membered residues after a treatment with TFA in 10 ml of DMF containing 0.046 ml (1 equivalent) of TEA under cooling with ice and the mixture was stirred overnight. The product was purified by the washing treatment followed by precipitation from DMF containing MeOH. The yield of the product having $R_{f1}$ of 0.77 was 1.45 g corresponding to 86% of the theoretical value.

(10) Preparation of Z(OMe)-Lys(Z)-Ala-Pro-Ser-Gly-Arg(Mts)-Met(O)-Ser(Bzl)-Ile-Val-Lys(Z)-Asn-Leu-Gln-Asn-Leu-Asp(OBzl)-Pro-Ser(Bzl)-His-Arg(Mts)-Ile-Ser-Asp(OChp)-Arg(Mts)-Asp(OChp)-Tyr(Cl$_2$-Bzl)-Met(O)-Gly-Trp(Mts)-Met(O)-Asp(OChp)-Phe-NH$_2$ (protected hCCK-33)

An azide form product (0.81 g or 5 equivalents) prepared from the fragment [7] in 5 ml of DMF and 0.038 ml (5 equivalents) of NMM was added to a solution of 1.20 mg (0.23 m mole) of the above mentioned peptideamide of 29-membered residues after a treatment with TFA in 5 ml of DMF containing 0.032 ml (1 equivalent) of TEA under cooling with ice and the mixture was stirred for 24 hours. The product was purified by the gel filtration method with Sephadex LH-60 followed by precipitation from DMF containing AcOEt. The yield of the product having $R_{f1}$ of 0.77 was 7.6 g.

TABLE 2

| Peptide protected with Z(OMe)- (sites) | Melting point °C. | $[\alpha]_D^{20}$ (DMF) | Empirical formula | Elementary analysis, calculated (found) | | |
|---|---|---|---|---|---|---|
| | | | | C | H | N |
| 14 residues (20-33) | 234-237 | -17.6° | C$_{144}$H$_{192}$N$_{24}$O$_{33}$S$_5$Cl$_2$H$_2$O | 55.96 (55.63 | 6.55 6.47 | 10.88 11.24 |
| 17 residues (17-33) | 230-232 | +8.9° | C$_{170}$H$_{221}$N$_{27}$O$_{39}$S$_5$Cl$_{26}$H$_2$O | 56.62 (56.59 | 6.51 6.33 | 10.49 10.61) |
| 22 residues (12-33) | 245-248 | -22.2° | C$_{195}$H$_{263}$N$_{35}$O$_{47}$S$_5$Cl$_{25}$H$_2$O | 56.15 (55.96 | 6.60 6.52 | 11.76 11.87) |
| 26 residues [1] (8-33) | 265-280 | -26.0° | C$_{230}$H$_{312}$N$_{40}$O$_{54}$S$_5$Cl$_{28}$H$_2$O | 56.65 (56.53 | 6.78 6.78 | 11.49 11.80) |
| 29 residues (5-33) | 260-262 | -8.0° | C$_{252}$H$_{346}$N$_{46}$O$_{60}$S$_7$Cl$_{26}$H$_2$O | 56.22 (56.01 | 6.70 6.35 | 11.97 12.22) |
| 33 residues (1-33) | 260-263 | -20.0° | C$_{277}$H$_{381}$N$_{51}$O$_{67}$S$_7$Cl$_{26}$H$_2$O | 56.38 (56.10 | 6.71 6.71 | 12.10 11.93) |

(11) H-Lys-Ala-Pro-Ser-Gly-Arg-Met-Ser-Ile-Val-Lys-Asn-Leu-Gln-Asn-Leu-Asp-Pro-Ser-His-Arg-Ile-Ser-Asp-Arg-Asp-Tyr-Met-Gly-Trp-Met-Asp-Phe-NH$_2$ (free hCCK-33)

Protected hCCK-33 (317 mg or 0.0547 m mole) in 3 ml of DMF was treated at room temperature for 60 minutes with 0.300 ml (30 equivalents) of phenylthio trimethyl silane and freed from the solvent by distillation followed by the addition of AcOEt to give 289 mg of a powder having $R_{f1}$ of 0.72. The yield was 89% of the theoretical value.

A reduced form of the protected hCCK-33 (100 mg or 0.0174 m mole) was treated with 1M TMSOTf-thioanisole in 5 ml of TFA for 2.5 hours in an ice bath in the presence of 0.244 ml (130 equivalents) of m-cresol and 0.033 ml (23 equivalents) of EDT and then admixed with dried ether. The thus obtained powder was dissolved in a mixture of 1 ml of MeOH and 2 ml of water under cooling with ice and the solution was admixed with 0.200 ml of 2-mercaptoethyl alcohol and 0.600 ml (36 equivalents) of 1M $NH_4F$. The pH of the solution was adjusted to 8.0 with TEA and, after 30 minutes of interruption, to 6.0 with 1N AcOH. The solution freed from a small amount of insoluble matter by centrifugation was introduced into a column of Sephadex G-25 having an inner diameter of 3.3 cm and a length of 105 cm and elution was performed with 1N AcOH. The fractions of No. 30 to No. 44 of each 8.0 ml volume corresponding to the front main peaks were collected under monitoring by the ultraviolet measurement at a wavelength of 280 nm and freed from the solvent by freeze drying to give 64.2 mg of a powdery product corresponding to a yield of 95.4% of the theoretical value.

In the next place, the thus obtained crude powder was subjected to ion-exchange chromatography through a column of CM-Trisacryl M having an inner diameter of 2.0 cm and length of 4.2 cm and passed through a mixing flask containing 250 ml of a 1M $NH_4HCO_3$ buffer solution having a pH of 7.9 followed by elution under a linear gradient formed with 250 ml of a 0.2M $NH_4HCO_3$ buffer solution having a pH of 7.9. The fractions No. 24 to No. 31 of each 8.2 ml volume corresponding to the main peaks were collected under monitoring by the UV measurement at 280 nm and freed from the solvent by freeze drying to give 20.1 mg of a fluffy powder corresponding to a yield of 31.1% of the theoretical value.

Further purification was undertaken by the reversed-phase HPLC on a Synchropak RPP column having an inner diameter of 4.0 cm and length of 25 cm by the elution with a gradient of MeCN in a 0.1% aqueous solution of TFA from 25% to 35% for 30 minutes at a flow rate of 1.0 ml/minute.

The eluate fractions corresponding to the main peaks shown in FIG. 7a having a retention time of 37 minutes as detected by the UV measurement at 280 nm were collected and freed from the solvent by freeze drying to give 10.6 mg of a fluffy powder corresponding to a 53% yield, of which $[\alpha]_D^{20}$ was $-65.7°$ (C=0.1; 0.5N AcOH).

The purified peptide was subjected to HPLC (see FIG. 7b, retention time 27 minutes) with a linear gradient (40 to 45% within 30 minutes) of MeCN in 1% TFA at a flow rate of 1.0 ml/minute through a YMC AN-302-ODS column having an inner diameter of 4 mm and length of 150 mm to give a single peak. FAB-MS m/z: 3864.4(M+H)+(calculated value as $D_{167}H_{264}N_{51}O_{49}S_3$: 3864.9)

The amino acid composition in the hydrolysis product with a 5N-hydrochloric acid is shown in Table 1 and the contents of the amino acids in the LAP digest are as shown below with the theoretical values given in the respective brackets: Asp 3.62(4); Ser 4.53(4); Pro 1.66(2); Gly 2.13(2); Ala 1.18(1); Val 1.10(1),; Met 2.70(3); Ile 2.28(2); Leu 2.44(2); Tyr 1.12(1); Phe 1.00(1); Lys 2.14(2); His 1.08(1); Trp 0.99(1); and Arg 3.24(3). Asn and Gln were not determined. Recovery of Phe was 77%.

FIG. 7 is an elution diagram obtained in the HPLC purification of unsulfated hCCK-33.

SIMULATION EXPERIMENTS (1) Fmoc protection and deprotection of Lys

H-Lys-OH (14.6 mg or 0.1 m mole) in 2 ml of $H_2O$-DMF (1:9) was treated with 141 mg (4 equivalents) of Fmoc-OSu in the presence of 59 μl (4 equivalents) of TEA for 60 minutes in an ice bath. In the course of the treatment, the starting material and the mono-Fmoc derivative having $R_f$ of 0.42 disappeared in the TLC and a new spot corresponding to $R_f$ of 0.66 and negative to the ninhydrin reaction appeared. After evaporation of the solvent, the product was dissolved in AcOEt or other organic solvent and washed successively with 5% citric acid, 5% $NaHCO_3$ and $H_2O$-NaCl and the solution was dehydrated over anhydrous $Na_2SO_4$ and freed from the solvent by evaporation. The residue was isolated by recrystallization or precipitation from a suitable solvent. The diFmoc derivative thus isolated was dissolved in 1 ml of DMF and the solution was treated with 1 ml (10 equivalents) of 1M $Bu_4NF$ in THF in the presence of 39 μl of EDT (10 equivalents) for 60 minutes at 25° C. The compound having $R_f$ of 0.66 was completely converted into H-Lys-OH having the same $R_f$ as at the starting point.

Z(OMe)-Tyr-OMe in 2 ml of DMF was similarly treated with 4 equivalents of Fmoc-OSu and TEA (4 equivalents) in the absence or presence of phenol for 60 minutes in a cold bath. The test by the TLC scanner indicated 7.8% formation or absolutely no formation of Z(OMe)-Tyr(Fmoc)-OMe having $R_f$ of 0.98, respectively. These results support the effectiveness of addition of phenol in suppressing denaturation of Tyr. Similarly, almost no formation of Z(OMe)-His(Fmoc)-OMe was noted in the treatment of 0.1 m mole of Z(OMe)-His-OMe with Fmoc-OSu and TEA.

Fmoc-Lys(Fmoc)-OH (0.1 m mole) in 2 ml of DMF-pyridine (8:2) containing 10 equivalents of a pyridine-$SO_3$ complex was kept at 25° C. for 18 hours not to show any detectable changes by the TLC.

(2) Selective $tBuPh_2$-silylation of Ser-OH

In the first place, the stability of the silylated Z(OMe)-Ser-OMe derivative was examined by the treatment with a pyridine-$SO_3$ complex. Z(OMe)-Ser-OMe (14 mg, 0.05 m mole) in 1 ml of DMF was treated with 10 equivalents of R-Cl, in which R is $Me_3Si$, $tBuMe_2Si$ or $tBuPh_2Si$, for 60 minutes in an ice bath in the presence of 20 equivalents of imidazole. The solvent was distilled off and the residue was washed with n-hexane. Each of the products (each 0.068 m mole) having $R_f$ of 0.97 and 0.99 for $Me_3Si$ and $tBuMe_2Si$, respectively, as R was dissolved in 1 ml of DMF-pyridine (8:2) containing 20 μl of EDT and admixed with 94 mg (10 equivalents) of a pyridine-$SO_3$ complex. Each of the solutions was kept at 25° C. and periodically inspected with a TLC scanner.

The $Me_3Si$ compound was completely desilylated within 30 minutes and about 15% of the $tBuMe_2Si$ compound was desilylated within 24 hours while the $tBuPh_2Si$ compound remained unchanged even after 24 hours.

In the next place, the selective $tBuPh_2$-silylation of Ser-OH was examined in the presence of Try-OH. A mixture of 0.05 m mole of Z(OMe)-Ser-OMe, 0.05 m mole of Z(OMe)-Tyr-OMe and 20 equivalents of imidazole was dissolved in 1 ml of DMF and treated with 20 equivalents of $tBuPh_2SiCl$ for 4 hours at 4° C. in the absence or presence of 20 equivalents of a phenolic compound which was phenol, m-cresol or p-methylthiophenol. Each of the products was subjected to quantitative analysis by a TLC scanner to give the results shown in Table 3.

At a moment of 4 hours after the start of the reaction at 25° C., 75% and 44% of the Z(OMe)-Tys-OMe had been silylated in the absence and presence, respectively, of phenol.

(3) Deprotection of tBuPh2Si groups from Z(OMe)-Ser(t-BuPh2Si)-OMe

Z(OMe)-Ser(t-BuPh2Si)-OMe (36 mg, 68μ moles) in 1 ml of DMF was treated with 1 ml of a 1M Bu4NF solution (15 equivalents) in DMF for 60 minutes at 25° C. in the presence of 20 μl of EDT. The starting material having $R_{f1}$ of 0.99 completely disappeared in the course of the treatment and a spot having $R_{f1}$ of 0.91 was detected corresponding to Z(OMe)-Ser-OMe.

(4) Sulfation of Tyr-OH

Z(OMe)-Ser-OMe and Z(OMe)-Tyr-Ome each in an amount of 0.05 m mole in 1 ml of DMF containing 20% of pyridine was treated with 5 equivalents of a pyridine-SO3 complex or 10 equivalents of PAS, respectively, at 25° C. and the reaction mixtures were inspected periodically using a TLC scanner. The results are shown in FIG. 4.

Z(OMe)-Trp-OH, Z(OMe)-Met-OH and Z(OMe)-His-OMe each in an amount of 0.05 m mole were similarly treated with a pyridine-SO3 complex or PAS for 4 hours. The former two remained unchanged whereas Z(OMe)-His-OMe was sulfated to the extent of 32% by the pyridine-SO3 complex and 18% by the PAS. The sulfated His compound having $R_{f1}$ of 0.21 was decomposed within 60 minutes by the addition of water at a pH of 6.0 to regenerate the starting material having $R_{f1}$ of 0.68.

(5) Conversion of unsulfated hCCK-33 into sulfated hCCK-33

Fmoc-OSu (79 mg, 30 equivalents) was added to an ice-chilled solution of 30 mg (7.8μ moles) of unsulfated hCCK-33 and phenol (22 mg, 30 equivalents) in 1 ml of DMF-H2O (9:1) containing 33 μl of TEA (30 equivalents) and the mixture was stirred for 2 hours in an ice bath. Dehydrated ether was added thereto and the thus obtained powder was reprecipitated with ether from DMF. The thus obtained Fmoc derivative having $R_{f3}$ of 0.66 was dissolved in 2 ml of DMF together with 6.8 mg (120 equivalents) of imidazole and 88 mg (120 equivalents) of phenol and then admixed with 216 μl (120 equivalents) of tBuPh2Si-Cl followed by stirring of the solution for 14 hours at 4° C. The powder obtained by the addition of ether to the reaction mixture was reprecipitated with ether from DMF. The product having $R_{f3}$ of 0.77 was gel-filtrated using Sephadex LH-20 in a column of 4 cm inner diameter and 47 cm length and purified by elution with DMF. The objective fractions No. 21 to No. 29 each in a volume of 9.2 ml were collected and combined under monitoring by means of the ultraviolet absorption at 280 nm wavelength in a similar manner to the other purification procedures and freed from the solvent by evaporation.

The residue was dissolved in 1 ml of DMF containing 20% of pyridine followed by the addition of 22 μl (30 equivalents) of EDT and 124 mg (100 equivalents) of a pyridine-SO3 complex and the mixture was stirred for 24 hours at 25° C. The solution was, in the same manner as before, introduced into a column of Sephadex LH-20 having an inner diameter of 4 cm and length of 47 cm and eluted out with DMF. The objective fractions No. 20 to No. 24 were combined and the solution was concentrated to have a volume of about 1 ml. This solution was treated with 1.0 ml of 1M Bu4NF in 1.0 ml of DMF in the presence of 22 μl (30 equivalents) of EDT for 60 minutes in an ice bath and then for 60 minutes at room temperature. While under chilling with ice, the solution was admixed with 4 ml of 1M NH4HCO3 and centrifuged to remove the small amount of insoluble matter. The supernatant was introduced into a Sephadex G-10 column having an inner diameter of 2.4 cm and length of 49 cm and eluted with a 1M NH4HCO3 buffer solution having a pH of 8.2. The fractions No. 11 to No. 17 corresponding to the front main peaks each having a volume of 7.8 ml were combined and subjected to repeated freeze drying to remove the solvent together with the salt thus to give 19.2 mg of a white powder corresponding to 63.9% of the theoretical yield.

Then, the crude sample was subjected to ion-exchange chromatography by introducing into a column of CM-Trisacryl M having an inner diameter of 1.6 cm and length of 4.5 cm and eluting hy the method of gradient elution with a gradient formed by 500 ml of a 0.2M NH4HCO3 buffer solution having a pH of 8.4 passing through a mixing flask containing 300 ml of a 0.01M NH4HCO3 buffer solution having a pH of 7.6. The fractions No. 21 to No. 29 corresponding to the second peak shown in FIG. 8a each having a volume of 7.8 ml were combined and subjected to repeated freeze drying to remove the solvent and the salt thus to give 7.5 mg of a powdery product corresponding to 39.1% of the theoretical yield and 25.0% of the overall yield.

The product thus obtained was further purified by HPLC using a column of Asahi Pak ODS-50 having an inner diameter of 10 mm and a length of 250 mm by the method of isocratic elution with a 31% MeCN solution in 0.1M AcONH4 having a pH of 6.5 at a flow rate of 2 ml per minute. The objective eluate fractions corresponding to the retention time of 42 minutes (see FIG. 8b) were combined and freed from the solvent by freeze drying to give 4.1 mg of a fluffy powder corresponding to 61% of the theoretical yield and overall yield of 15% based on the unsulfated hCCK-33. When the silylation reaction was performed for 3 hours at 25° C., the yield after similar purification treatments was 13%. The product of $R_{f2}$ 0.42 had $[\alpha]^{21}_D$ of $-72.7°$ (C=0.1, H2O). The retention time by the HPLC was 14 minutes in the elution (see FIG. 8c) through a column of Asahipak ODP-50 having an inner diameter of 4 mm and length of 150 mm at a flow rate of 1 ml/minute using a gradient of MeCN from 20 to 40% within 30 minutes in 0.1M AcONH4 having a pH of 7.8. The amino acid composition in the 6N HCl-hydrolysis product was as shown in Table 1. The amino acid composition in the LAP digest was as shown below with the theoretical values shown in the respective brackets: Asp 3.49(4); Ser 4.22(4); Pro 1.50(2); Gly 2.12(2); Ala 1.13(1),; Val 1.14(1); Met 2.92(3); Ile 1.96(2); Leu 2.07(2); Tyr(SO3H) 0.91(1); Phe 1.00(1); Lys 2.00(2); His 0.92(1); Trp 0.96(1); and Arg 2.87(3). Asn and Gln were not detected. The recovery of Phe was 81%. The Asp-Pro bond was resistant against the action of the used LAP.

What is claimed is:

1. A method for the modification of a polypeptide containing a Tyr residue and either Ser or Tyr, or both, which comprises the successive steps of:
   (a) protection of the polypeptide amine groups with a base labile protective group;

(b) the selective protection of the Ser or Thr hydroxyl groups with tert-butyl diphenylsilyl whereby the copresence of phenol further prevents the modification of the Tyr hydroxyl group;

(c) sulfating the hydroxyl group on the Tyr residues.

2. A method for the modification of a polypeptide as claimed in claim 1 in which the polypeptide as the starting material is human cholecystokinin (hCCK-33) in an unsulfated form expressed by the formula H—Lys—Ala—Pro—Ser—Gly—Arg—Met—Ser—Ile—Val—Lys—Asn—Leu—Gln—
Asn—Leu—Asp—Pro—Ser—His—Arg—Ile—Ser—Asp—Arg—Asp—Tyr—Met—Gly—
Trp—Met—Asp—Phe—NH$_2$.

3. A method for the preparation of a polypeptide as claimed in claim 1 in which the amino-protective group is a 9-fluorenylmethyl oxycarbonyl (Fmoc) group.

4. A method for the preparation of a polypeptide as claimed in claim 1 in which the amino group protected with an amino-protective group is deprotected before reaction with trimethylsilyl trifluoromethane sulfonate (TMSOTf).

* * * * *